March 26, 1957 H. A. CONKLIN Plant Pat. 1,582
ROSE PLANT
Filed Dec. 22, 1955
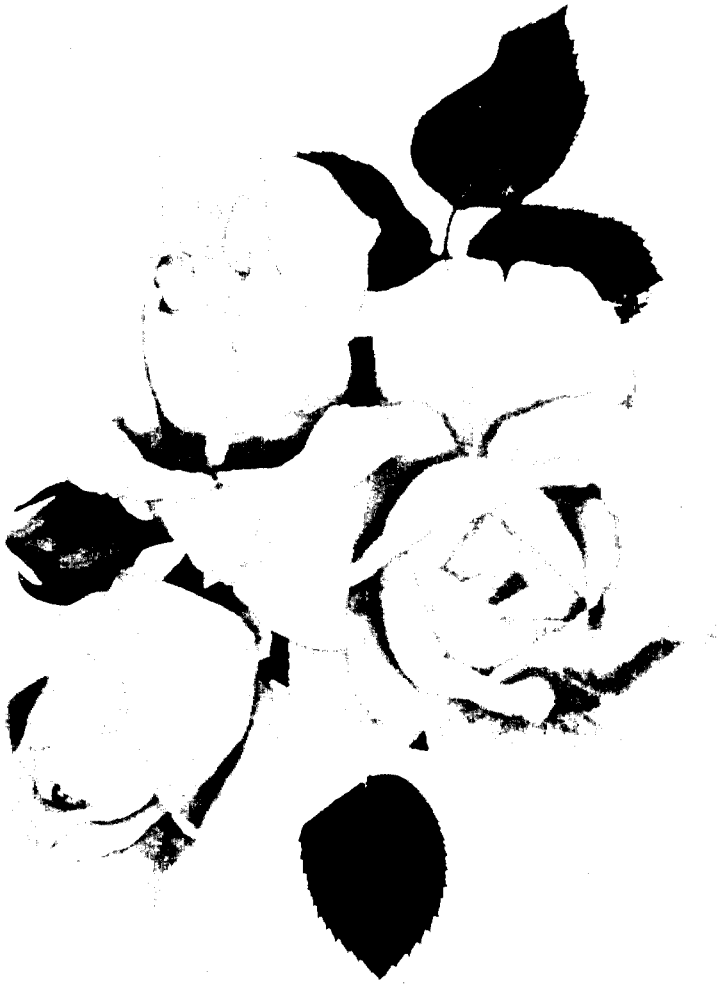
INVENTOR.
HENRY A. CONKLIN
BY J. F. Cuneo
ATTORNEY United States Patent Office Plant Pat. 1,582
Patented Mar. 26, 1957

1,582

ROSE PLANT

Henry A. Conklin, West Covina, Calif.

Application December 22, 1955, Serial No. 554,906

1 Claim. (Cl. 47—61)

This invention is directed to a new and distinct variety of rose plant which falls in the hybrid tea class.

The parent plant of the new variety of rose was discovered by me on my property located at 1204 Glendora Avenue in the city of West Covina, California, as a "sport" coming from a Red Radiance rose plant, an unpatented variety.

The flowers that are produced by the new variety of rose plant are so unique and distinctive that they attract instant attention. The blooms are strikingly similar to a variegated camelia in coloring, the petals of the flowers are best described as predominantly red streaked and splashed with white in varying amount. The colors of the blooms are not particularly affected by the sun and the blooms approach in size those of the Red Radiance rose. The flowers are produced in abundance during the growing season which normally extends from April to November, and have a lasting quality that persists even after the flowers have been cut. The petalage of the flower is double and the flowers are borne either singly or in clusters of from three to five on a fairly long stem.

In comparing the blooms of my new variety with those of the Red Radiance rose, the new variety is readily distinguishable by the variegated effect produced by the white streaked and splashed red petals. The red is generally described as a crimson red and is slightly lighter in color than the red of the Red Radiance rose. The blooms of the Red Radiance rose are solid red which as stated above is a little darker than the red of the new variety. The blooms of the new variety are best described as globular and double in petalage, having from 25 to 30 petals.

The unique and distinctive variegated effect of the flowers clearly distinguish it from the Red Radiance hybrid tea rose as well as from the other varieties in its class. The plant has been reproduced asexually by budding performed at West Covina, California. The plant and flowers with their distinguishing features reproduce true and the distinguishing features are transmitted through succeeding propagations of the variety. The plant will not reproduce true from seed.

The accompanying colored illustration shows a typical specimen group of the flower and foliage of the new variety of rose in various stages of development. The colors are as correct as it is possible to reproduce them by this type of representation.

A detailed description of the new variety follows, and to facilitate the identification of the important colors described in the specification, the terminology adopted in the British Horticultural Color Chart is followed.

The new rose belongs to the outdoor bush type, principally used for cut flowers and garden ornamentation. The rose belongs to the hybrid tea class. The rose retains its distinguishing characteristics through succeeding propagations by budding.

*The flower*

Locality where grown and observed: West Covina, California.

Flowers borne: Either singly or in clusters of from three to five on a stem approximately fourteen inches long.

Number of blooms: When grown outdoors the plant produces an abundant number of flowers.

Continuity: The plant blooms continuously throughout the blooming season which generally extends from April to November.

Fragrance: The flowers have a slight fragrance in warm weather which becomes more pronounced in cooler weather.

Bud:

*Peduncle.*—Length—average length one half inch, average caliper to heavy. Color—light green inside, darker green outside.

*Before calyx breaks.*—Size—medium, usually one half by five eights inches. Form—medium length; ovoid; usually with foliacious parts extending beyond the tip of the bud approximately one quarter the length of the bud and occasionally more.

*As calyx breaks.*—Color—slightly darker crimson than Chrysanthemum Crimson 824/3. Sepals—pointed; light green inside and dark green outside; the same colors are observed at the base.

*As first petal opens.*—Size—approximately one and three eighths inches by one and three eighths inches. Form—ovate with edges reflexed. Color: outside—red portion, Chrysanthemum Crimson 824/3; petal is generally streaked and/or splashed and/or speckled with white; inside—red portion, Chrysanthemum Crimson 824/3; petal is generally streaked and/or splashed and/or speckled with white; base of petal near attachment—a small area at the base is yellow.

*Opening.*—Opens up normally and is not affected abnormally by cold, hot, wet or dry atmospheric conditions.

Bloom:

*Size.*—Average; when fully open, from three to three and one half inches in diameter.

*Petalage.*—Number of petals and petaloids vary from 25 to 30, arranged regularly.

*Form.*—High centered and globular at first becoming open to cupped later, petals at first being cupped, with lateral margins of inner petals usually reflexed slightly from one fourth to one third or sometimes more, of the length of the petal. Apex of outer petals sometimes reflexed one fourth to one third of the petal length. Petals at maturity become flat-cupped with lateral margins of inner petals usually reflected one half or more of the upper portion of the petal; lateral margins of extreme outer petals sometimes reflected three quarters or more of the petal length.

*Petals.*—Texture—thick and leathery, with the inside of the petals having a somewhat velvety appearance and the outside of the petals having a satiny look. Shape: outside—broadly obovate, with average apex being substantially flat; a few notches are observed; intermediate—obovate with apex rounded to flat; inside—narrowly obovate, somewhat irregular with apex rounded.

This description of a newly opened flower was taken from a rose grown in the month of October, at West Covina, California:

*Color.*—Outside petals—Chrysanthemum Crimson, 824/3. The red is streaked and/or splashed and/or speckled with white. A small area of the petal at the base near attachment is yellow. The color of the inner and outer surfaces of the petal is substantially the same. Intermediate petals—Chrysanthemum Crimson, 824/3. The red is streaked and/or splashed and/or speckled with white. A small area of the petal at the base near attachment is yellow. The coloring of the inner and outer surfaces of the intermediate petals is substantially the same. Inner petals—Chrysanthemum Crimson, 824/3. The red is streaked and/or splashed and/or speckled with white. A small area of the petal at the base near attachment is yellow. The coloring of the inner and outer surfaces of the inner petals is substantially the same.

A flower that had been open for three days outdoors, in the month of October, at West Covina, California, had substantially the same color and appearance as a newly opened flower.

The flower has the following general characteristics:

*General color effect.*—Newly opened flower is Chrysanthemum Crimson, 824/3. The red is streaked, splashed and speckled with white; a small area at the base of the petals is yellow. A three day old flower has the same general color effect.

*Behavior.*—Petals drop off cleanly. The flower is not inordinately affected by hot, cold, wet or dry atmospheric conditions.

*Flower longevity.*—Cut roses grown outdoors and kept at normal room temperature last from three to five days in the month of October. Flowers on the bush in the garden, during the month of October last from five to seven days.

*Reproductive organs*

Stamens: Average number of stamens varies from 25 to 30. These are arranged regularly about the pistils.

Filaments: Filaments are of medium length, about one quarter inch long. Color—Nepal Red, 330/32.

Anthers: Anthers are medium size, all open at approximately the same time. Color: upper—lemon yellow; underside—lemon yellow.

Pollen: Pollen is moderate to abundant. Color—lemon yellow.

Pistils: Pistils average from 40 to 50 in number.

Styles: The styles are moderately even; average length about one quarter inch; average caliper and bunched. Color—lemon yellow.

Stigma: Color—the color is best described as Salmon Orange.

Ovaries: The ovaries are usually all enclosed in the calyx.

Hips:

*Length.*—Average length.

*Form.*—Ovoid generally, about one quarter by one quarter inch; slightly pear shaped.

*Colors.*—Dark green changing when mature to yellow.

Sepals: The sepals are permanent and of medium length, somewhat curled and recurved. Color—dark green outside and somewhat lighter inside.

Seeds: The seeds are of average size and number from one to five.

*The plant*

Foliage:

*Leaves.*—Compound of an average of five leaflets; normal to abundant in quantity. Ovate in shape; approximately one and one eighth inches wide and one and three quarters inches long; leathery; dark green and glossy. Margins are serrate.

*Leaflets.*—Shape—ovoid with apex acute; base is round and margins are simply serrate. Color: mature—the upper surface is dark green with the lower side light green; young leaves—have the same color as mature leaves.

*Rachis.*—Average size; upper and lower sides are smooth with stipitate glands not prominent.

*Stipules.*—Not prominent.

Growth:

*Habit.*—Bushy upright and much branched. Plant grows from two to three feet in height.

*Growth.*—Hardy and vigorous.

*Canes.*—Medium caliper. Main stems—about eighteen inches long; color—light green in color. Prickles—approximately one quarter inch in length; substantially straight; color—varies from reddish to dark brown. Hairs—none. Small prickles—several; color—varies from reddish to dark brown.

*Branches.*—Color—light green. Shape—predominantly vertical. Hairs—none. Small prickles—average number about 20 prickles to an eighteen inch stem.

*New shoots.*—Color—light red. Large prickles—about 8 prickles to an eight inch stem. Small prickles—none on an eight inch stem.

Having thus described my invention I claim:

The new and distinct variety of rose plant of the class designated as hybrid tea roses, substantially as herein shown and described, characterized particularly as to novelty by the distinctive variegated effect produced by the predominantly Chrysanthemum Crimson blooms that are streaked, splashed and speckled with white, the medium size and abundance of its blooms throughout the growing season, the excellent petal substance and lasting quality of the blooms, the double petalage of the blooms, and its medium long flower stem.

No references cited.